United States Patent
Jones et al.

(10) Patent No.: US 8,540,763 B2
(45) Date of Patent: Sep. 24, 2013

(54) DETACHABLE SELF-EXPANDING ANEURYSM COVER DEVICE

(75) Inventors: Donald K. Jones, Dripping Springs, TX (US); Vladimir Mitelberg, Austin, TX (US)

(73) Assignee: DePuy Synthes Products, LLC, Raynham, MA (US)

( * ) Notice: Subject to any disclaimer, the term of this patent is extended or adjusted under 35 U.S.C. 154(b) by 976 days.

(21) Appl. No.: 11/903,463

(22) Filed: Sep. 21, 2007

(65) Prior Publication Data

US 2008/0039930 A1 Feb. 14, 2008

Related U.S. Application Data

(63) Continuation-in-part of application No. 10/465,975, filed on Jun. 27, 2003, now abandoned.

(51) Int. Cl.
*A61F 2/06* (2013.01)

(52) U.S. Cl.
USPC .......................................................... 623/1.17

(58) Field of Classification Search
USPC ............. 606/108; 623/1.11–1.12, 1.15, 1.17, 623/1.39–1.4
See application file for complete search history.

(56) References Cited

U.S. PATENT DOCUMENTS

| | | | |
|---|---|---|---|
| 4,512,338 A | 4/1985 | Balko | |
| 4,994,071 A | 2/1991 | MacGregor | |
| 5,108,407 A | 4/1992 | Geremia | |
| 5,122,136 A | 6/1992 | Guglielmi | |
| 5,147,370 A | 9/1992 | McNamara et al. | |
| 5,176,626 A | 1/1993 | Soehendra | |
| 5,197,978 A | 3/1993 | Hess | |
| 5,288,711 A | 2/1994 | Mitchell | |
| 5,336,163 A | 8/1994 | DeMane | |
| 5,354,308 A | 10/1994 | Simon et al. | |
| 5,454,788 A * | 10/1995 | Walker et al. | 604/96 |
| 5,484,444 A | 1/1996 | Braunschweiler et al. | |
| 5,514,176 A | 5/1996 | Bosley, Jr. | |
| 5,516,781 A | 5/1996 | Morris | |
| 5,551,954 A | 9/1996 | Buscemi | |
| 5,562,725 A | 10/1996 | Schmitt et al. | |
| 5,563,146 A | 10/1996 | Morris | |
| 5,591,195 A | 1/1997 | Taheri et al. | |
| 5,643,309 A | 7/1997 | Myler | |
| 5,643,339 A | 7/1997 | Kavteladze et al. | |
| 5,646,160 A | 7/1997 | Morris | |
| 5,665,728 A | 9/1997 | Morris | |
| 5,667,486 A | 9/1997 | Mikulich et al. | |
| 5,716,396 A | 2/1998 | Williams, Jr. | |
| 5,728,131 A | 3/1998 | Frantzen | |
| 5,772,668 A | 6/1998 | Summers | |
| 5,800,520 A | 9/1998 | Fogarty et al. | |
| 5,836,966 A | 11/1998 | St. Germain | |
| 5,893,887 A | 4/1999 | Jayaraman | |
| 6,165,195 A | 12/2000 | Wilson et al. | |
| 6,254,612 B1 | 7/2001 | Hieshima | |

(Continued)

*Primary Examiner* — Ryan Severson
*Assistant Examiner* — Ashley Cronin

(57) ABSTRACT

A self-expanding aneurysm cover device which takes the form of an outwardly biased cylindrical skeletal frame in which the proximal end of the cylindrical skeletal frame forms a loop which extends at an oblique angle to the axis of the cylindrical skeletal frame. A positioning tab extends from the proximal end of the skeletal frame which when pulled causes the cylindrical skeletal frame to collapse to a reduced diameter for removal of the device from a vessel.

5 Claims, 3 Drawing Sheets

(56) References Cited

U.S. PATENT DOCUMENTS

| | | |
|---|---|---|
| 6,267,783 B1 | 7/2001 | Letendre |
| 6,344,055 B1 | 2/2002 | Shukov |
| 6,413,272 B1 * | 7/2002 | Igaki ............................. 623/1.15 |
| 6,468,301 B1 * | 10/2002 | Amplatz et al. .............. 623/1.13 |
| 6,569,190 B2 * | 5/2003 | Whalen et al. ................. 623/1.1 |
| 6,936,058 B2 | 8/2005 | Forde |

\* cited by examiner

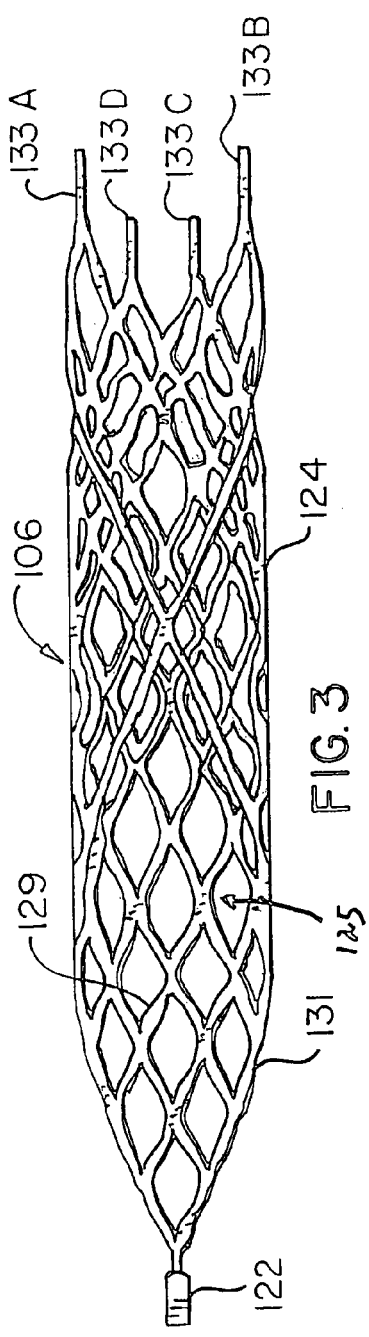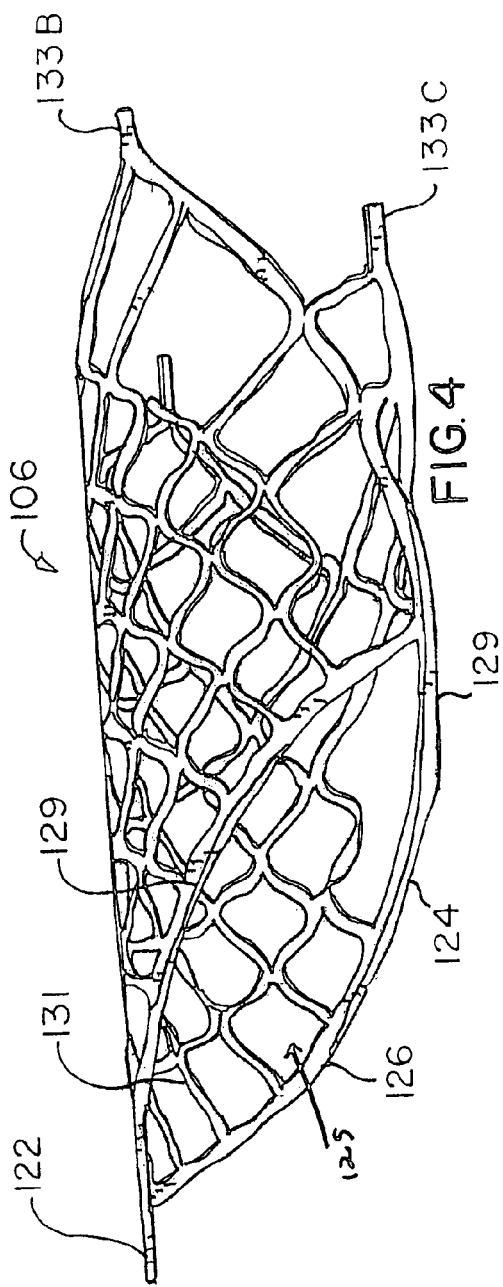

DETACHABLE SELF-EXPANDING ANEURYSM COVER DEVICE

CROSS-REFERENCE TO RELATED APPLICATION

The present application is a continuation-in-part of Ser. No. 10/465,975, entitled "Detachable Self-Expanding Aneurysm Cover Device", filed Jun. 27, 2003 now abandoned.

BACKGROUND OF THE INVENTION

1. Field of the Invention

The present invention relates to a repositionable self-expanding intravascular aneurysm cover device and a hydraulic deployment system for placing the device at a preselected location within a vessel of the human body, and more particularly, relates to a device and hydraulic deployment system for the device which may be used to initially place the aneurysm cover device at a first location within a vessel and if it is desirable to reposition the device, the device may be withdrawn into the deployment system and subsequently repositioned at a different location.

2. Description of the Prior Art

For many years flexible catheters have been used to place various devices within the vessels of the human body. Such devices include dilatation balloons, stents, embolic coils and aneurysm covers. Examples of such catheter devices are disclosed in U.S. Pat. No. 5,108,407, entitled, "A Method And Apparatus For Placement Of An Embolic Coil"; U.S. Pat. No. 5,122,136, entitled, "Endovascular Electrolytically Detachable Guidewire Tip For The Electroformation Of Thrombus In Arteries, Veins, Aneurysms, Vascular Malformations And Arteriovenous Fistulas." These patents disclose devices for delivering an embolic coil to a preselected position within a vessel of the human body in order to treat aneurysms, or alternatively, to occlude the blood vessel at the particular location.

Devices, such as stents, which are placed in vessels may take the form of helically wound wire, or tubular like structures, with numerous patterns defining the walls. Examples of various stent configurations are disclosed in U.S. Pat. No. 4,512,338, entitled, "Process For Restoring Patentcy To Body Vessels"; U.S. Pat. No. 5,551,954, entitled, "Biodegradable Drug Delivery Vascular Stent"; and U.S. Pat. No. 4,994,071, entitled, "Bifurcating Stent Apparatus And Method." Stents are generally formed of materials which retain their shape under the pulsatile flow conditions encountered when placed within the body vessel. Some materials that have been used to make such stents include metals and alloys, such as, stainless steel, tantalum, tungsten and nitinol, as well as polymers such as polyvinyl alcohol (PVA), polyglycolic acid (PGA) and collagen. On occasion multiple stents are placed at a given location to provide the desired vascular support.

In the past, the deployment of stents has been accomplished by numerous techniques. One such technique used to deploy a typical wire stent uses a pusher wire to push the wire stent through the lumen of a properly positioned cannula. As the stent exits the cannula it takes a predetermined shape until completely deposited in the vessel. This procedure is usually conducted under fluoroscopic visualization, such that the movement of the stent through the vasculature can be monitored. With these placements systems there is very little control over the exact placement of the stent since the stent may be ejected to a position some distance beyond the end of the cannula. As is apparent, with these latter systems, when the stent has been released from the cannula it is difficult, if not impossible, to retrieve the stent or to reposition the stent.

Numerous procedures have been developed to enable more accurate positioning of stents within a vessel. One such procedure utilizes a helically wound wire loop stent with a relaxed diameter. The stent is wound on a smaller diameter delivery while fixing the ends of the stent. This keeps the stent in a small diameter, tightly wound coil. This system is then delivered through the lumen of a properly positioned catheter exiting at a desired location. Once the delivery wire is activated to release the ends of the stent, the stent radially expands to its relaxed larger diameter. Such a stent positioning method is disclosed in U.S. Pat. No. 5,772,668, entitled, "Apparatus For Placing An Endoprosthesis."

Another stent positioning system utilizes a self-expanding tubular stent. This stent has a relaxed diameter that approximates the diameter of the vessel to be supported. For transport through the catheter, the stent is positioned on a smaller diameter delivery wire. A sheath is positioned over the stent/delivery wire assembly constraining the stent to a smaller diameter. Once the assembly is placed at the desired location in the vasculature, the sheath is withdrawn exposing the stent allowing the stent to return to its predetermined larger size. The expansion of the stent uncouples the stent from the delivery wire while depositing the stent in the vessel at the desired location.

Still another stent positioning system utilizes a hydraulic stent deployment system for placing a self-expandable stent into the vessels of the body, and in particular into the small vessels of the brain. More particularly, this stent positioning system utilizes a catheter having a distal tip for retaining the stent in order to transport the stent to a predetermined position within a vessel and a control mechanism for releasing the stent at the preselected position. The control mechanism generally takes the form of a pressure generating device, such as a syringe, which is used to apply pressure to the catheter to thereby cause the distal end of the catheter to expand radially which in turn causes the stent to be released from the distal tip of the catheter. An example of such a stent positioning system is illustrated in U.S. Pat. No. 6,254,612, entitled, "Hydraulic Stent Deployment Systems," and assigned to the same assignee as the present invention.

An example of a self-expanding tubular stent is illustrated in U.S. Pat. No. 6,267,783, entitled, "Stent Which Is Easily Recaptured And Repositioned Within The Body." This self-expanding stent is formed by cutting and removing diamond shaped sections from the wall of a thin-walled nitinol tube to thereby form a relatively flexible, skeletal, tubular stent. The stent may be compressed to a smaller size for insertion into a vessel and then may be permitted to expand to a size where the stent contacts the walls of a vessel. The disclosed stent may also be recaptured and repositioned within a vessel.

An example of a self-expanding aneurysm cover is shown in U.S. Pat. No. 5,591,195 entitled, "Apparatus And Method For Engrafting A Blood Vessel." The aneurysm cover illustrated in this patent is comprised of an expandable wire frame, which upon expansion, supports a fabric material which covers the mouth of an aneurysm.

SUMMARY OF THE INVENTION

The present invention is directed toward a deployment system and a aneurysm cover device which may be delivered at a site within a vessel and may be withdrawn after placement and to reposition the device at another site within the vessel.

In accordance with one aspect of the present invention, the self-expanding aneurysm cover device deployment system also includes a delivery catheter through with the device is delivered to the predetermined location. Initially, the device is retained by the deployment catheter within a delivery catheter and the device is positioned within the lumen of the distal section of the delivery catheter. The deployment catheter and the delivery catheter are moved to a desired position within a vessel and the deployment catheter is moved distally to permit the device to be pushed out of the distal end of the delivery catheter. The aneurysm cover device, being a self-expanding device, expands radially and contacts the walls of the vessel. If, prior to the final release of the aneurysm cover device from the deployment catheter it is determined that the device should be repositioned to another position within the vessel, the deployment catheter may be moved proximally back into the delivery catheter. As the aneurysm cover device is withdrawn into the delivery catheter, the device collapses to fit within the lumen of the delivery catheter. Once the device has been withdrawn into the delivery catheter, the delivery catheter may be moved into another position within the vessel for repositioning and subsequent release of the device. Accordingly, with this aneurysm cover device design is possible to permit the self-expanding device to completely expand at a first location, to then withdraw the device back into the delivery catheter, to move the delivery catheter to a second position and to again expand the device at the second position for subsequent release of the device.

In accordance with another aspect of the present invention, the self-expanding aneurysm cover device includes a generally cylindrical skeletal frame in which the frame includes a proximal loop portion, a positioning tab attached to the proximal loop portion and extending from the loop portion in a direction generally parallel to the longitudinal axis of the skeletal frame, and also includes a distal spring biased portion connected to the loop portion along at least two spaced apart locations on the loop portion. The skeletal frame is adapted to assume a first expanded position in which the spring portion is expanded to thereby cause the loop portion to be expanded to form a generally cylindrical loop configuration which lies in a plane extending in an oblique angle to the longitudinal axis of the skeletal frame. When the tab is moved proximally, the skeletal frame becomes compressed so that the loop portion lies in a plane extending closer to parallel to the longitudinal axis of the skeletal frame thereby causing the spring-biased portion to collapse which in turn causes the loop portion to collapse for easy withdrawal of the aneurysm cover device from a vessel.

In accordance with still another aspect of the present invention, the self-expandable aneurysm cover device includes an outwardly biased cylindrical skeletal frame in which the skeletal frame defines a proximal loop portion which lies in a plane extending at an oblique angle to the longitudinal axis of the cylindrical skeletal frame. The cover device also includes a positioning tab attached to the proximal end of the skeletal frame such that when force is applied to the positioning tab to cause the tab to move in a direction proximally of the cylindrical skeletal frame, the frame is caused to collapse radially for easy removal of the aneurysm cover device from a vessel.

In accordance with still another aspect of the present invention, the aneurysm cover device includes a generally cylindrical frame having a first condition in which said cylindrical skeletal frame may be compressed to have an overall small outside diameter and a normally biased second condition in which the cylindrical skeletal frame has an overall larger diameter. The cylindrical skeletal frame defines a loop portion at its proximal end in which the loop portion lies in a plane extending at an oblique angle to the longitudinal axis of the cylindrical skeletal frame. Also the device includes a positioning tab attached to the loop portion and extending from the proximal end of the loop portion in a direction generally parallel to the longitudinal axis of the skeletal frame. When a pulling force is applied to the positioning tab in a direction proximal to the cylindrical frame, the cylindrical frame is caused to collapse to form a device which has a reduced outside diameter therefore which may be easily removed from a vessel.

In accordance with another aspect of the present invention, the deployment system includes an elongated flexible deployment catheter having a distal section for retaining the aneurysm cover device so the device may be moved to a preselected position within the vessel. The catheter has a lumen which extends throughout the length of the catheter and also includes a distal section which is formed of a material having a durometer such that when sufficient fluid pressure is applied to the interior of the deployment catheter, the walls of the distal tip expand outwardly, or radially, to thereby increase the size of the lumen at the distal section of the catheter. A headpiece element, or protruding tab, of the aneurysm cover device is placed into the lumen at the distal section of the catheter and is retained by the distal section of the catheter. A hydraulic injector, such as a syringe, is coupled to the proximate section of the catheter for applying a fluid pressure to the interior of the catheter. When the device is placed at the desired position within the vessel, fluid pressure is applied to the interior of the deployment catheter by the hydraulic injector to thereby cause the walls of the distal section to expand outwardly thereby releasing the device for placement in the vessel.

BRIEF DESCRIPTION OF THE DRAWINGS

FIG. 3 is an enlarged elevational view of the aneurysm cover device shown in FIG. 2 when viewed from the bottom;

FIG. 4 is an enlarged oblique view of the aneurysm cover device as shown in FIG. 2;

DESCRIPTION OF THE PREFERRED EMBODIMENT

Figure 1:
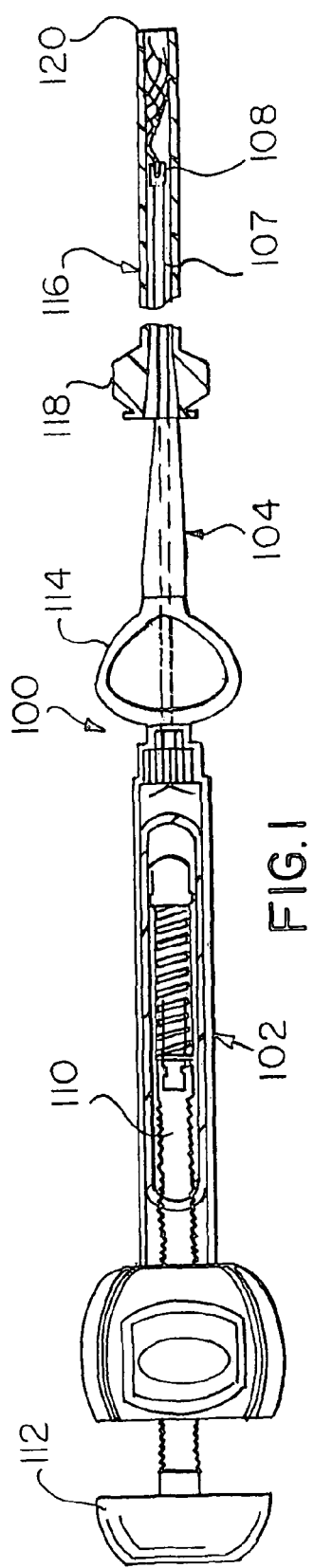
FIG. 1 is an enlarged, partially sectioned view of an embodiment of the hydraulic deployment system and aneurysm cover device in accordance with the present invention.

FIG. 1 generally illustrates the intravascular aneurysm cover device deployment system 100 which is comprised of a hydraulic injector or syringe 102, coupled to the proximal end of a deployment catheter 104. An intravascular aneurysm cover device is disposed within the lumen of the distal section 108 of the catheter 104. The proximal end of the aneurysm cover device is tightly held within the lumen of the distal section 108 of the catheter 104 until the deployment system is activated for release of the aneurysm cover device. As may be seen, the syringe 102 includes a threaded piston 110 which is controlled by a handle 112 for infusing fluid into the interior of the catheter 104. Also as illustrated, the catheter 104 includes a winged hub 114 which aids in the insertion of the catheter into the access catheter 116 which has a proximal hub 118 that is placed in the vascular system of the body. The intravascular aneurysm cover device deployment system 100 is described in more detail in U.S. Pat. No. 6,254,612, entitled, "Hydraulic Stent Deployment System" and assigned to the assignee of the present invention. This patent and the disclosure thereof is incorporated herein by reference.

Figure 2:
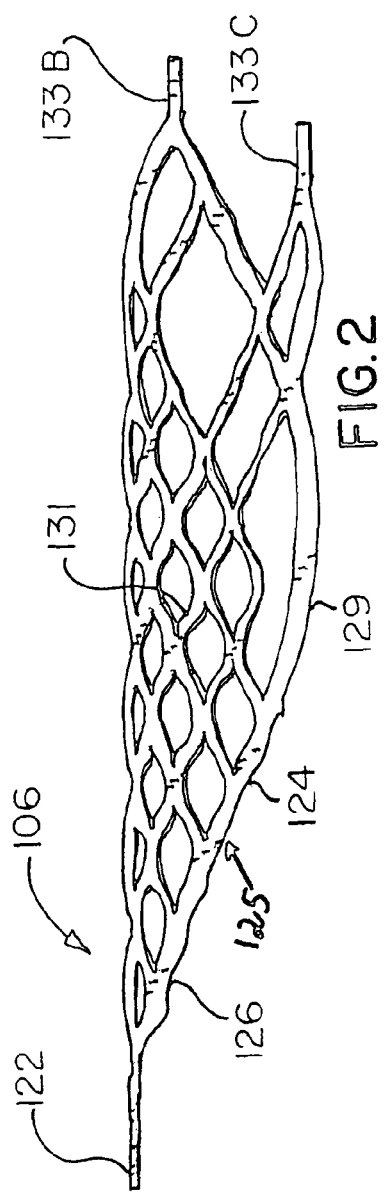
FIG. 2 is an enlarged elevational view showing the aneurysm cover device of the present invention in an expanded configuration.

FIGS. 2, 3 and 4 illustrate in more detail the intravascular self-expanding aneurysm cover device. The aneurysm cover device is comprised of a headpiece element 122 which extends from the proximal end of a self-expanding skeletal tubular section 124.

The tubular section 124 is preferably formed from a thin-walled cylindrical tube formed from a super elastic alloy of nickel and titanium, such as nitinol. A description of medical devices which utilize such alloys may be found in U.S. Pat. No. 4,665,906, entitled, "Medical Devices Incorporating Sim Alloy Elements," which is hereby incorporated by reference. The tubular section 124 is preferably laser cut from a nitinol tube and thereafter treated so as to exhibit super elastic properties at body temperature. As illustrated, tubular section 124 is formed by removing diamond patterned sections from the sidewalls of the nitinol tube, and when the aneurysm cover device is fully expanded, the diamonds would have angles of between 20 and 70 degrees at their distal and proximal ends. As is apparent, the tubular section 124 may be formed with various other patterns or configurations.

Also, and as illustrated in FIGS. 2 through 4 subsequent to cutting the diamond patterned sections from the tubular section 124, the proximal end of the tube is cut to form a loop configuration 125 which extends in a plane which is oblique to the longitudinal axis of the tubular section 124. This angle is preferably between about 10 and 70 degrees to the longitudinal axis of the aneurysm cover device. The preferred angle is 20 degrees to the longitudinal axis. After the diamond patterned sections are cut, there is formed a continuous proximal oval shaped loop 126. The headpiece element 122 is connected to the most proximal edge of the proximal oval shaped loop 126. The headpiece element 122 is retained by the deployment catheter 104. FIGS. 2 through 4 illustrate the aneurysm cover device in its normal or expanded state prior to insertion into a delivery catheter for insertion into a vessel of the body.

As may be noted in FIGS. 2 and 4, the pattern is constructed such that the diamonds which are in the lower portion of this Figure, i.e., diamonds on opposite side of aneurysm cover device from the portion of the aneurysm cover device which covers the aneurysm, are larger in size than the diamonds in the upper portion of this Figure which results in a denser mesh existing in the portion of the aneurysm cover device which covers the aneurysm.

As also may be noted in FIG. 2 and FIG. 4, the aneurysm cover device includes outer struts 129 which are cut of a wider thickness than the inner struts 131 which causes the outer structure of the aneurysm cover device to provide a more rigid structure for holding the aneurysm cover device into the vessel and across the aneurysm. The rigid outer struts 129 also provide additional rigidity to improve "pushability" of the aneurysm cover device through the delivery catheter 128.

As further noted in FIG. 3, the aneurysm cover device includes four radiopaque markers 133*a*, 133*b*, 133*c* and 133*d* which aide in the positioning of the aneurysm cover device across an aneurysm. The radiopaque markers 133*a* through 133*d* are preferably formed by electroplating the distal portions of the struts with a radiopaque material, such as gold. As may be observed in FIGS. 2 and 3, the radiopaque markers 133*d* and 133*c* do not extend distally as far as marker 133*a* and 133*d*. The longer markers 133*a* and 133*b* provide an indication of the more dense (upper portion of FIG. 2) portion of the aneurysm cover device to thereby aide in placement of the aneurysm cover device across the aneurysm in two respects. The longer markers 133*a* and 133*b* assist in placing the more dense portion of the aneurysm cover device at a position across the aneurysm and also provide an indication of the width of the more dense portion of the aneurysm cover device relative to the aneurysm.

As may be appreciated the aneurysm cover device may be delivered using various types of delivery systems other than the hydraulic delivery system disclosed in the present patent application. Such other devices may use heat, electric or mechanical systems to release the aneurysm cover device into a vessel with or without other embolic devices, such as embolic coils.

The aneurysm cover device may be treated by applying a coating to reduce the occurrence of a stenosis or to improve compatibility with other embolic devices. An example of a coating to reduce the occurrence of a stenosis is rapamycine. U.S. Pat. Nos. 5,288,711; 5,516,781; 5,563,146; 5,646,160 and 5,665,728 all disclose techniques for applying this coating to medical devices. The disclosures of these patents are incorporated by reference herein. In addition, the aneurysm cover device may be covered by a fabric covering, such as a polymer mesh, to more completely seal the opening of an aneurysm.

Figure 5:
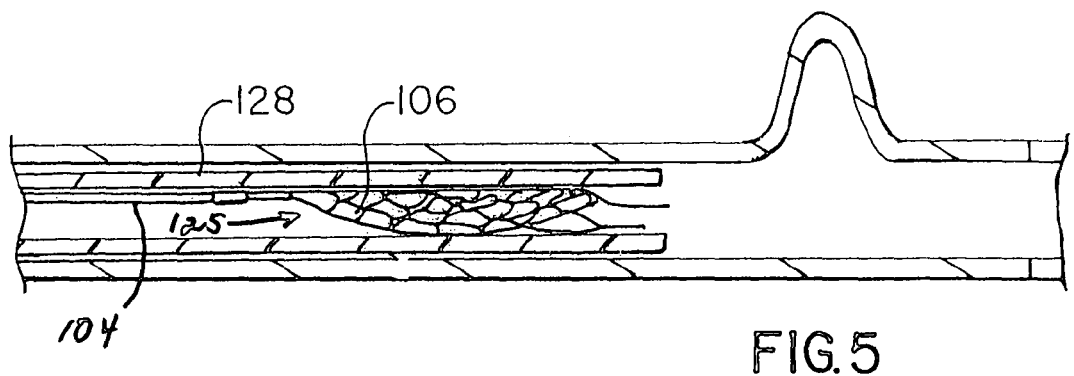
FIG. 5 illustrates the aneurysm cover device of the present invention positioned within a delivery catheter prior to delivery of the aneurysm cover device into a vessel.
Figure 6:
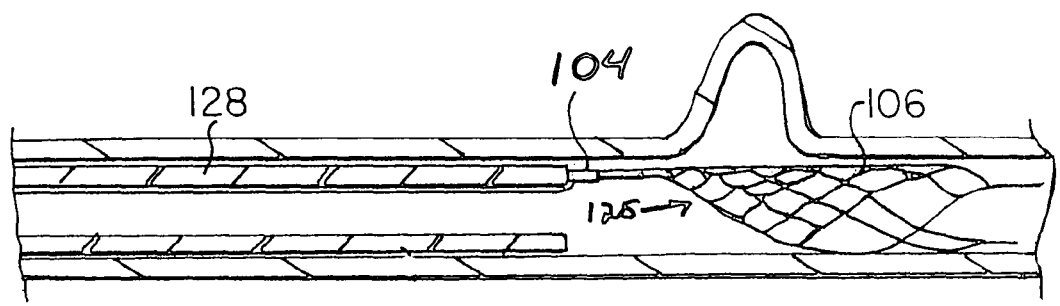
FIG. 6 is an enlarged partially sectioned view illustrating the aneurysm cover device of FIG. 5 after expansion of the device in a vessel; and, FIG. 7 is an enlarged partial sectioned view illustrating the aneurysm cover device partially withdrawn into the delivery catheter and partially collapsed for subsequent repositioning within a vessel.
Figure 7:
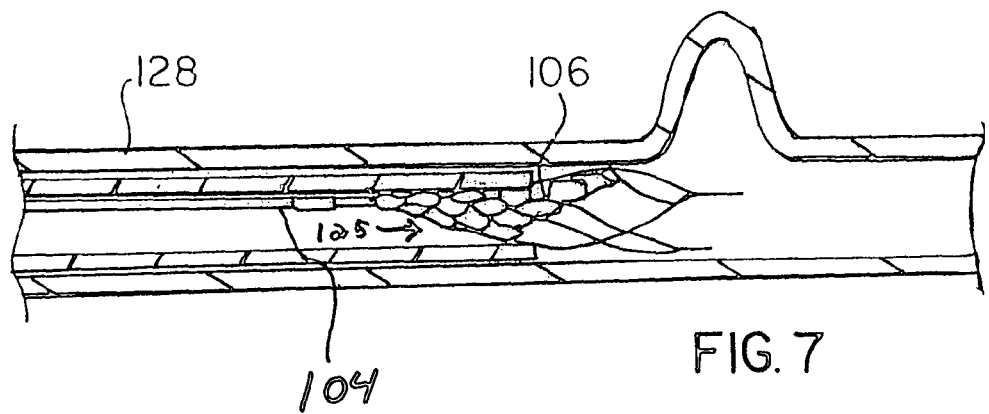

As illustrated in FIG. 5, the self-expanding aneurysm cover device is placed within a delivery catheter 128 which serves to compress the aneurysm cover device to a size sufficiently small so that it may be inserted into a vessel and across an aneurysm. As may be noted in FIG. 5, upon compression, the proximal loop portion 125 of the tubular section 124 is caused to move into a plane which extends closer to parallel to the longitudinal axis of the tubular section 124. Once the delivery catheter 128 is properly positioned within a vessel adjacent the aneurysm, the deployment catheter 104 may be moved distally relative to the delivery catheter, or alternatively the delivery catheter 128 may be moved proximally relative to the deployment catheter 104, thereby causing the aneurysm cover device to move out of the distal end of the delivery catheter and thereafter expand into contact with the walls of the vessel and across the neck of the aneurysm. At this point the hydraulic deployment system may be actuated to release the aneurysm cover device. Alternatively, if the aneurysm cover device is not positioned at a correct location, the deployment catheter 104 may be withdrawn proximally relative to the delivery catheter to thereby withdraw the aneurysm cover device back into the delivery catheter. As the aneurysm cover device is withdrawn into the catheter it collapses to fit within the distal portion of the delivery catheter 128. After the aneurysm cover device is withdrawn back into the delivery catheter 128, the delivery catheter may be moved into a new position and the aneurysm cover device may once again be deployed.

As may be noted, because of the construction of the aneurysm cover device which results in the proximal edge of the device lying in a plane which is oblique to the longitudinal axis of the device, the device collapses easily as the device is withdrawn back to the delivery catheter 128. If this edge, or loop 126, were to be positioned at right angles to the longitudinal axis of the aneurysm cover device, as is the case with prior art devices, it would be very difficult, if not impossible, to withdraw the device back into the delivery catheter 128 once the device had been moved entirely out of the distal end of the catheter. The "ramp" configuration at the proximal edge of the aneurysm cover device 106 of the present invention causes the aneurysm cover device to collapse easily within the delivery catheter 128 thereby providing a device which may be very easily repositioned after initially being placed at a selected location.

Although a particular embodiment of the present invention has been shown and described, modifications may be made to the device and/or method of use without departing from the spirit and scope of the present invention. The terms used in describing the invention are used in their descriptive sense and not as terms of limitations.

That which is claimed is:

1. A self-expandable aneurysm cover device comprising:
a generally cylindrical skeletal frame having a longitudinal axis, said frame including a proximal loop portion at the proximal end of said skeletal frame which extends in a plane between opposite sides of said generally cylindrical skeletal frame, which is oblique to the longitudinal axis of the skeletal frame and which has a proximal edge, an elongated headpiece attached to the proximal edge of the proximal loop portion and extending from said proximal edge of the proximal loop portion in a direction generally parallel to the longitudinal axis of the skeletal frame, said skeletal frame being adapted to assume a normal first expanded condition to thereby cause said loop portion to be expanded to form a loop configuration which lies in the plane extending at an oblique angle to the longitudinal axis of said skeletal frame and to cause said skeletal frame to take the form of a generally cylindrical configuration, and upon moving the elongated headpiece in a proximal direction said proximal loop portion is caused to move to a position such that the plane of the loop portion is closer to parallel to the longitudinal axis of the skeletal frame thereby causing the skeletal frame to collapse for easy withdrawal of the aneurysm cover device from a vessel, and
wherein the cylindrical skeletal frame includes outer struts and inner struts, the inner struts forming a connecting mesh extending between the outer struts, said outer struts being larger in cross section than said inner struts, and wherein the spacing between the inner struts in a generally central region of said mesh is much less than the spacing of the inner struts in portions of the skeletal frame near the outer struts.

2. The self-expandable aneurysm cover device as defined in claim 1, wherein the proximal loop portion of the generally cylindrical skeletal frame lies in the plane which extends about 10 to 70 degrees to the longitudinal axis of the cylindrical skeletal frame when the skeletal frame is in the normal first expanded condition.

3. The self-expandable aneurysm cover device as defined in claim 2, wherein the proximal loop portion of the generally cylindrical skeletal frame lies in the plane which extends about 20 degrees to the longitudinal axis of the cylindrical skeletal frame when the skeletal frame is in the normal first expanded condition.

4. A method of placing and then repositioning a self-expandable aneurysm cover device which includes a generally cylindrical skeletal frame in which the cylindrical skeletal frame defines a loop portion at its proximal end, the loop portion normally lies in a plane extending between opposite sides of the cylindrical skeletal frame and at an oblique angle to a longitudinal axis of the cylindrical skeletal frame, a headpiece is attached to the loop portion and extends from the proximal end of the loop portion in a direction generally parallel to the longitudinal axis of the skeletal frame, and wherein the cylindrical skeletal frame includes outer and inner struts, the inner struts forming a connecting mesh with the outer struts, said outer struts being larger in cross section than said inner struts, wherein the spacing between the inner struts in a generally central region of said mesh is much less than the spacing between the inner struts in portions of the skeletal frame near the outer struts, the method comprising the steps of:
inserting into a vessel the aneurysm cover device which is compressed and carried within a lumen of a delivery catheter;
positioning the aneurysm cover device at a preselected position within a vessel;
moving the headpiece of the aneurysm cover device distally to cause the device to move completely out of the lumen of the catheter thereby causing the device to completely expand into contact with the walls of the vessel; and,
moving the headpiece of the aneurysm cover device proximally through the lumen of the delivery catheter to thereby cause the loop portion which is normally in a plane oblique to the longitudinal axis of the skeletal frame to move into the plane closer to parallel to the longitudinal axis of the skeletal frame to thereby cause the aneurysm cover device to collapse into the lumen of the catheter to permit repositioning of the device to another position within the vessel.

5. The method as defined in claim 4, wherein the spacing between the inner struts on said opposite side of the skeletal frame is much less than the spacing between the outer struts on said one of said sides of the skeletal frame, and when the cylindrical skeletal frame is positioned at its desired location relative to the aneurysm which it is to cover, the inner struts overlie the aneurysm.

\* \* \* \* \*